United States Patent
Bates et al.

(10) Patent No.: US 9,300,612 B2
(45) Date of Patent: Mar. 29, 2016

(54) MANAGING INTERACTIONS IN A VIRTUAL WORLD ENVIRONMENT

(75) Inventors: Cary Lee Bates, Rochester, MN (US); Jim Chun-Ta Chen, Rochester, MN (US); Zachary Adam Garbow, Rochester, MN (US); Gregory Edward Young, South St. Paul, MN (US)

(73) Assignee: International Business Machines Corporation, Armonk, NY (US)

( * ) Notice: Subject to any disclaimer, the term of this patent is extended or adjusted under 35 U.S.C. 154(b) by 2104 days.

(21) Appl. No.: 12/354,054

(22) Filed: Jan. 15, 2009

(65) Prior Publication Data

US 2010/0180216 A1 Jul. 15, 2010

(51) Int. Cl.
| | |
|---|---|
| *G06F 3/048* | (2013.01) |
| *H04L 12/58* | (2006.01) |
| *A63F 13/75* | (2014.01) |
| *A63F 13/30* | (2014.01) |
| *H04N 7/15* | (2006.01) |
| *H04L 29/06* | (2006.01) |
| *A61B 5/00* | (2006.01) |
| *A63F 9/24* | (2006.01) |
| *H04M 1/725* | (2006.01) |

(52) U.S. Cl.
CPC .............. *H04L 51/12* (2013.01); *A63F 13/12* (2013.01); *A63F 13/75* (2014.09); *H04L 12/585* (2013.01); *H04L 67/38* (2013.01); *H04N 7/157* (2013.01); *A61B 5/744* (2013.01); *A63F 9/24* (2013.01); *A63F 2300/556* (2013.01); *A63F 2300/5553* (2013.01); *A63F 2300/572* (2013.01); *H04M 1/72544* (2013.01); *H04M 2203/1025* (2013.01)

(58) Field of Classification Search
CPC ....... H04L 51/12; H04L 12/585; H04L 67/38; A63F 13/00; A63F 13/75; A63F 9/24; A63F 13/12; A63F 2300/572; A63F 2300/5553; A63F 2300/556; H04N 7/157; A61B 5/744; H04M 1/72544; H04M 2203/1025
USPC .......................................................... 715/757
See application file for complete search history.

(56) References Cited

U.S. PATENT DOCUMENTS

| | | | | |
|---|---|---|---|---|
| 8,026,918 | B1 * | 9/2011 | Murphy ................. | G06N 3/006 345/473 |
| 8,099,668 | B2 * | 1/2012 | Garbow ................. | A63F 13/12 705/319 |
| 8,312,511 | B2 * | 11/2012 | Garbow ............. | H04L 63/1441 463/29 |
| 8,713,450 | B2 * | 4/2014 | Garbow ................ | G06F 21/316 705/325 |
| 2004/0111479 | A1 * | 6/2004 | Borden ................ | G06Q 10/107 709/206 |
| 2009/0049513 | A1 * | 2/2009 | Root ....................... | G06F 21/53 726/1 |
| 2009/0079816 | A1 * | 3/2009 | Qvarfordt .......... | G06K 9/00335 348/14.16 |
| 2009/0113554 | A1 * | 4/2009 | Zalewski ................ | A63F 13/12 726/26 |

(Continued)

OTHER PUBLICATIONS

Humphrey Cheung, "A chat with a World of Warcraft bot programmer," Dec. 2005.*

(Continued)

*Primary Examiner* — Patrick Riegler
(74) *Attorney, Agent, or Firm* — Patterson & Sheridan, LLP

(57) ABSTRACT

Methods and apparatus associate a computed trust level to avatars that interact with one another in a simulated environment. The avatars may represent legitimate users of the virtual world or spammers. System monitoring of each avatar provides ability to recognize potential spammers and create an alternate indication of the spammers. A user index may be used to store data describing attributes of each avatar for analysis using programs stored in memory.

19 Claims, 5 Drawing Sheets

(56) References Cited

U.S. PATENT DOCUMENTS

| | | | | |
|---|---|---|---|---|
| 2009/0132689 A1* | 5/2009 | Zaltzman | G06Q 10/00 709/223 |
| 2009/0276718 A1* | 11/2009 | Dawson | A63F 13/10 715/753 |
| 2010/0023879 A1* | 1/2010 | Finn | A63F 13/12 715/757 |
| 2010/0081508 A1* | 4/2010 | Bhogal | A63F 13/12 463/40 |

OTHER PUBLICATIONS

Yahoo Answers, "How do report someone on World of Warcraft?" 2007.*

Jason Rice, "World of Warcraft: Blizzard Planning on Implementing New Span-Prevention Features," May 2007.*

Wikia WoWWiki, "Ignore list," May 2008.*

Curse.com, "Friend & Ignore Share," Oct. 2008.*

WoWWiki, "Addon Comm Throttling," Apr. 29, 2008, http://www.wowwiki.com/Addon_Comm_Throttling.*

* cited by examiner

MANAGING INTERACTIONS IN A VIRTUAL WORLD ENVIRONMENT

BACKGROUND OF THE INVENTION

1. Field of the Invention

Embodiments of the invention relate to evaluation of an avatar within an immersive virtual environment.

2. Description of the Related Art

A virtual world is a simulated environment in which users may inhabit and interact with one another via avatars. Users may also interact with virtual objects and locations of the virtual world. An avatar generally provides a graphical representation of an individual within the virtual world environment. Avatars are usually presented to other users as two or three-dimensional graphical representations that resemble a human individual. Frequently, virtual worlds allow multiple users to enter the virtual environment and interact with one another. Virtual worlds are said to provide an immersive environment, as they typically appear similar to the real world and objects tend to follow rules related to gravity, topography, locomotion, physics and kinematics. Of course, virtual worlds can suspend or alter these rules as well as provide other imaginative or fanciful environments. Users typically communicate with one another through their avatars using, for example, text messages sent between avatars, real-time voice communication, gestures displayed by avatars, and symbols visible in the virtual world.

Virtual worlds may be persistent. A persistent world provides an immersive environment (e.g., a fantasy setting used as a setting for a role-playing game, or a virtual world complete with land, buildings, towns, and economies) that is generally always available, and world events happen continually, regardless of the presence of a given avatar. Thus, unlike more conventional online games or multi-user environments, the virtual world continues to exist, and plot and events continue to occur as users enter (and exit) the virtual world.

The virtual world provides an opportunity for a spammer to create avatars for navigating the virtual world to, for example, promote products or places. Such spamming in the virtual world may be disruptive for other avatars as well as pose risks to participants and companies within the virtual world.

SUMMARY OF THE INVENTION

In one embodiment, a method of monitoring for spammers includes assigning an initial trust rank to a new avatar upon the new avatar creating an account on a system linked to a network that enables communication with other avatars. The method further includes adjusting the initial trust rank to a computed trust rank based on actions of the new avatar. In addition, disabling the account of the new avatar occurs when the computed trust rank reaches a threshold set to identify the new avatar as a spammer.

For one embodiment, a computer readable medium contains a program which, when executed, performs an operation to monitor for spammers that includes assigning an initial trust rank to a new avatar upon the new avatar creating an account on a system linked to a network that enables communication with other avatars. The operation performed also adjusts the initial trust rank to a computed trust rank based on actions of the new avatar. Further, the operation performed by program disables the account of the new avatar when the computed trust rank reaches a threshold set to identify the new avatar as a spammer.

According to one embodiment, a method of monitoring for spammers includes providing a system linked to a network that enables communication between first and second avatars. The method includes monitoring the first avatar including an interaction between the first and second avatar and assigning an adjustment value based on the interaction between the first and second avatar. Further, changing a trust ranking of the first avatar occurs based on the adjustment value.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Figure 1:
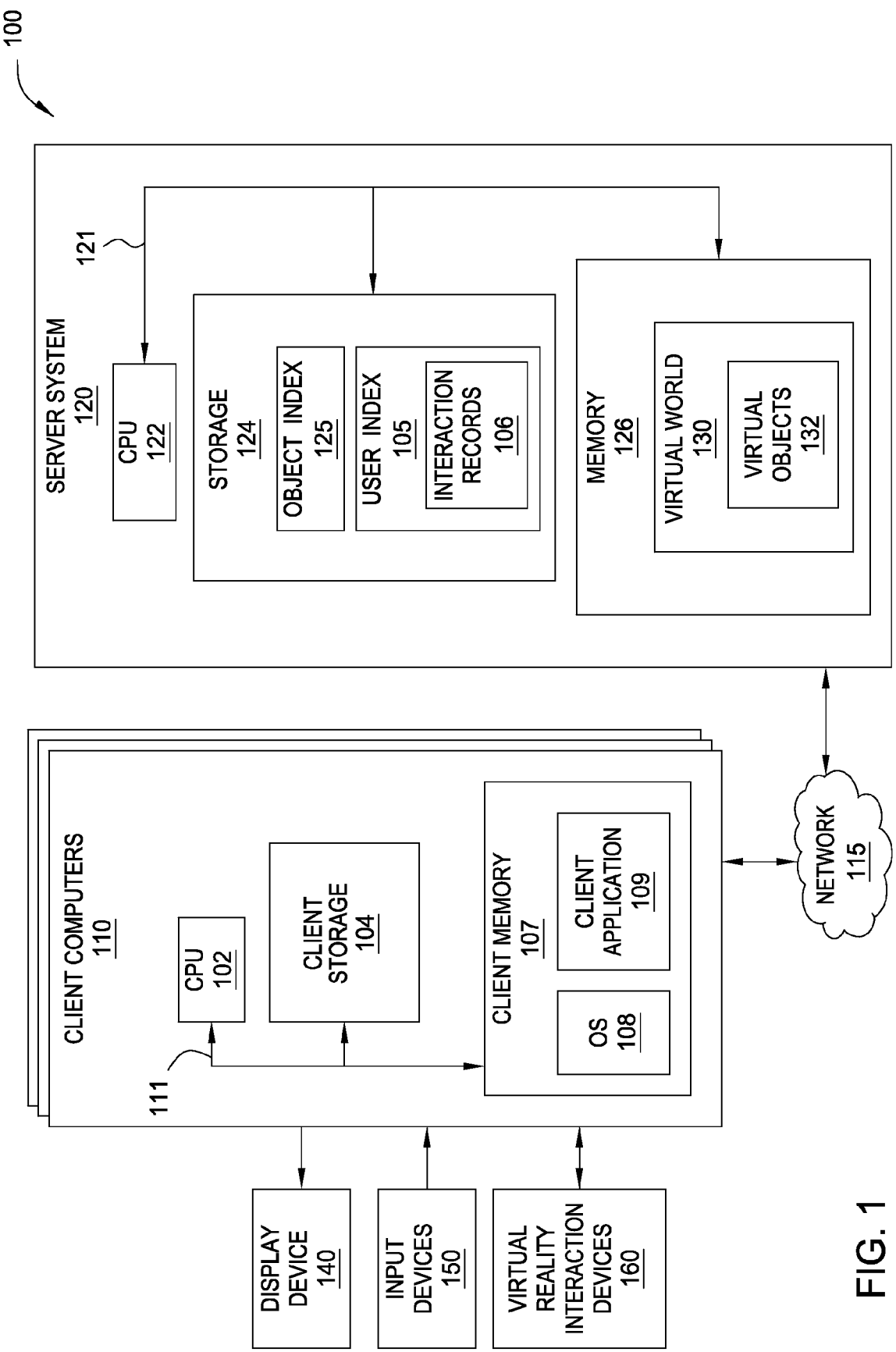
FIG. 1 is a block diagram that illustrates a client server view of a computing environment configured for displaying avatars and monitoring the avatars in a virtual world, according to one embodiment of the invention.

As stated above, virtual world is a simulated environment in which users may inhabit and interact with one another via avatars. The avatars may represent legitimate users of the virtual world or spammers. A "spammer" generally refers to an avatar controlled by a user (or computer program) in a manner so as to be disruptive to users of the virtual environment. Most commonly, the spamming avatar is used to deliver unsolicited commercial messages to users of the virtual environment. In real life, people can judge one another based on actual attributes that often cannot be readily disguised making it possible to evaluate trustworthiness with some level of confidence. Applying a trust level to the avatars enables identifying trustworthiness even in the virtual world.

The trust level predicts probability of the avatar being a spammer and thereby enables the legitimate user to recognize the avatar of another legitimate user compared to the avatar of the spammer. A ranking algorithm may assign the trust level based on actions, conversations, and/or dialogue of the avatar being monitored. In practice, a user index may be used to store data describing attributes of each avatar for analysis using programs that are stored in memory and that execute the ranking algorithm. Monitoring avatars in the virtual world provides an ability to identify and police actions of spammers within the virtual world.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

One embodiment of the invention is implemented as a program product for use with a computer system. The program(s) of the program product defines functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

FIG. 1 shows a block diagram that illustrates a client server view of computing environment 100, for one embodiment. As shown, the computing environment 100 includes client computers 110, network 115 and server system 120. In one embodiment, the computer systems illustrated in FIG. 1 are included to be representative of existing computer systems, e.g., desktop computers, server computers, laptop computers, and tablet computers. The computing environment 100 illustrated in FIG. 1, however, is merely an example of one computing environment. Embodiments of the invention may be implemented using other environments, regardless of whether the computer systems are complex multi-user computing systems, such as a cluster of individual computers connected by a high-speed network, single-user workstations, or network appliances lacking non-volatile storage. Further, the software applications illustrated in FIG. 1 and described herein may be implemented using computer software applications executing on existing computer systems, e.g., desktop computers, server computers, laptop computers, and tablet computers. However, the software applications described herein are not limited to any currently existing computing environment or programming language, and may be adapted to take advantage of new computing systems as they become available.

In one embodiment, the server system 120 includes a central processing unit (CPU) 122, which obtains instructions and data via a bus 121 from memory 126 and storage 124. The processor 122 could be any processor adapted to support the methods of the invention. The memory 126 is any memory sufficiently large to hold the necessary programs and data structures. The memory 126 can be one or a combination of memory devices, including Random Access Memory, non-volatile or backup memory, (e.g., programmable or Flash memories, read-only memories, etc.). In addition, the memory 126 and storage 124 may be considered to include memory physically located elsewhere in the server system 120, for example, on another computer coupled to the server system 120 via the bus 121. The server system 120 may be operably connected to the network 115, which generally represents any kind of data communications network. Accordingly, the network 115 may represent both local and wide area networks, including the Internet.

As shown, the memory 126 includes virtual world 130. In one embodiment, the virtual world 130 may be a software application that accepts connections from multiple clients, allowing users to explore and interact with an immersive virtual environment by controlling the actions of an avatar. Illustratively, the virtual world 130 includes virtual objects 132. The virtual objects 132 represent the content present within the environment provided by the virtual world 130, including both elements of the "world" itself as well as elements controlled by a given user. Illustratively, the storage 124 includes an object index 125, a user index 105, and interaction records 106. The object index 125 may store data describing characteristics of the virtual objects 132 included in the virtual world 130 and is accessed to perform searches of the virtual objects 132. In one embodiment, the user index 105 stores records describing the avatars, such as data regarding trust ranking of the avatars as determined based on the interaction records 106, which include data related to interactions between the avatars. In one embodiment, the trust ranking is assigned by the system against an arbitrary scale based on analysis described further herein.

As shown, each client computer 110 includes a CPU 102, which obtains instructions and data via a bus 111 from client memory 107 and client storage 104. The CPU 102 is a programmable logic device that performs all the instruction, logic, and mathematical processing in a computer. The client storage 104 stores application programs and data for use by the client computer 110. The client storage 104 includes, for example, hard-disk drives, flash memory devices, and optical media. The client computer 110 is operably connected to the network 115.

The client memory 107 includes an operating system (OS) 108 and a client application 109. The operating system 108 is the software used for managing the operation of the client computer 110. Examples of the OS 108 include UNIX, a version of the Microsoft Windows® operating system, and distributions of the Linux® operating system. (Note, Linux is a trademark of Linus Torvalds in the United States and other countries.)

In one embodiment, the client application 109 provides a software program that allows a user to connect to the virtual world 130, and once connected, to explore and interact with the virtual world 130. Further, the client application 109 may be configured to generate and display a visual representation, generally referred to as the avatar, of the user within the immersive environment. The avatar of the user is generally visible to other users in the virtual world, and the user may view avatars representing the other users. The client application 109 may also be configured to generate and display the immersive environment to the user and to transmit the user's desired actions to the virtual world 130 on the server 120. Such a display may include content from the virtual world determined from the user's line of sight at any given time. For the user, the display may include the avatar of that user or may be a camera eye where the user sees the virtual world through the eyes of the avatar representing this user.

Figure 2:
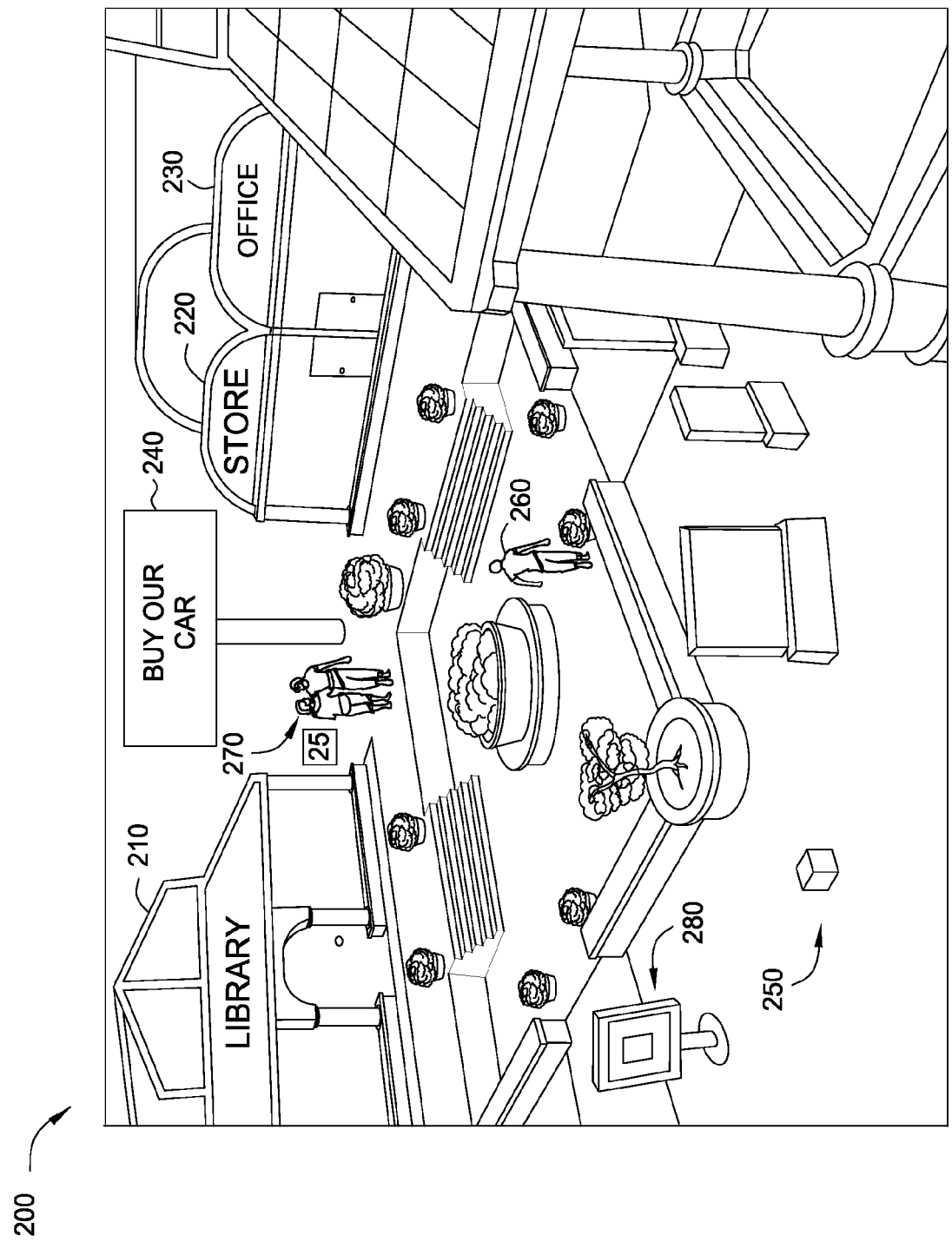
FIG. 2 illustrates an example display of a user participating via one of the avatars in the virtual world, according to one embodiment of the invention.

For instance, using the example illustrated in FIG. 2, the virtual objects 132 may include a box 250, a store 220, and a library 210. More specifically, FIG. 2 illustrates a user display 200 presenting a user with a virtual world, according to one embodiment. In this example, the user is represented by a first avatar 260, and another user is represented by a second avatar 270. Within the virtual world 130, avatars can interact with other avatars. For example, the user with the first avatar 260 can click on the second avatar 270 to start an instant message conversation with the other user associated with the second avatar 270. The user may interact with elements displayed in the user display 200. For example, the user may interact with the box 250 by picking it up and opening it. The user may also interact with a kiosk 280 by operating controls built into the kiosk 280 and requesting information. The user may also interact with a billboard 240 by looking at it (i.e., by positioning the line of sight directly towards the billboard 240). Additionally, the user may interact with larger elements of the virtual world. For example, the user may be able to enter the store 220, the office 230, or the library 210 and explore the content available at these locations.

The user may view the virtual world using a display device 140, such as an LCD or CRT monitor display, and interact with the client application 109 using input devices 150 (e.g., a keyboard and a mouse). Further, in one embodiment, the user may interact with the client application 109 and the virtual world 130 using a variety of virtual reality interaction devices 160. For example, the user may don a set of virtual reality goggles that have a screen display for each lens. Further, the goggles can be equipped with motion sensors that cause the view of the virtual world presented to the user to move based on the head movements of the individual. As another example, the user can don a pair of gloves configured to translate motion and movement of the user's hands into avatar movements within the virtual reality environment. Of course, embodiments of the invention are not limited to these examples and one of ordinary skill in the art will readily recognize that the invention may be adapted for use with a variety of devices configured to present the virtual world to the user and to translate movement/motion or other actions of the user into actions performed by the avatar representing that user within the virtual world 130.

Figure 3:
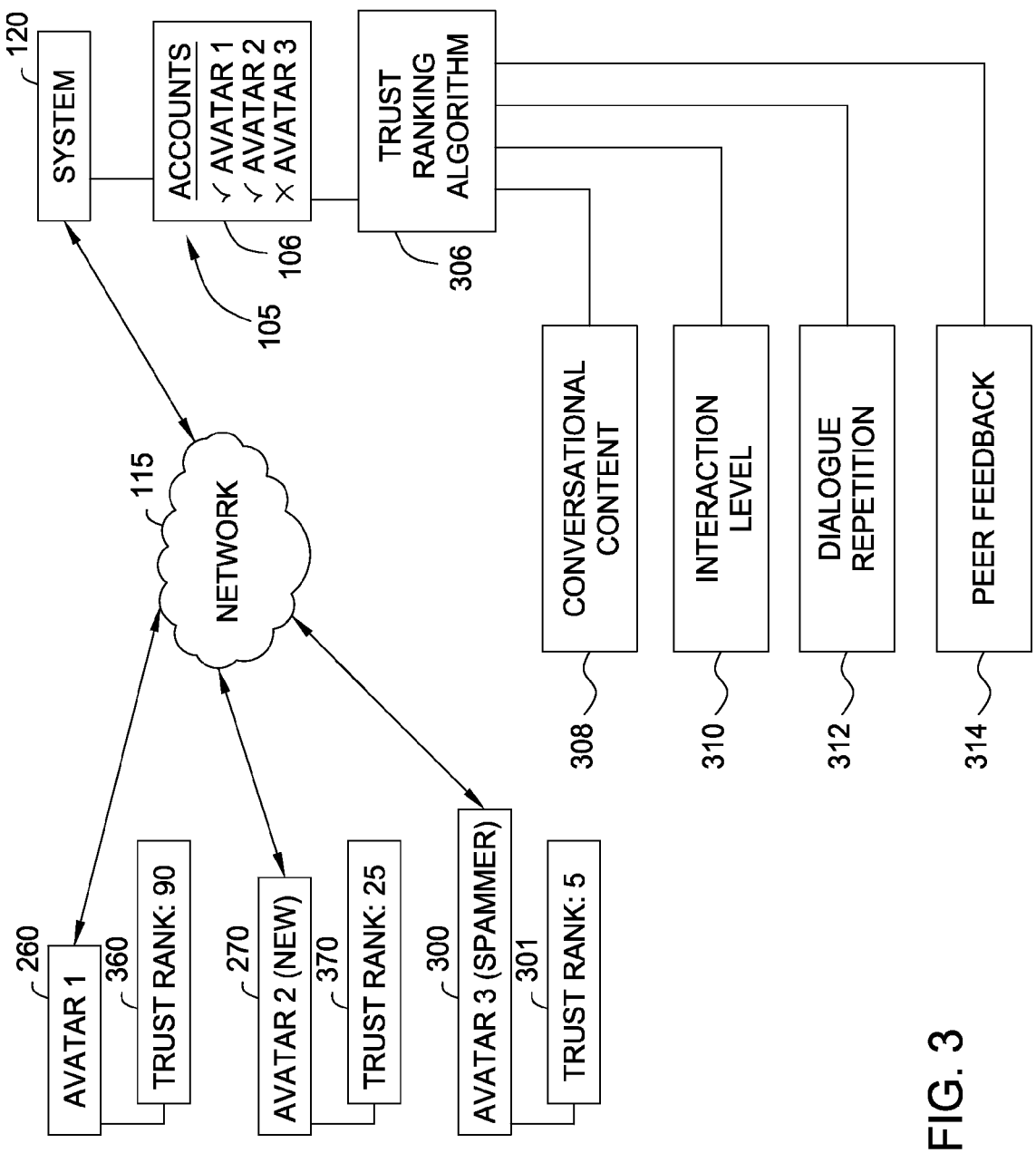
FIG. 3 is a schematic diagram showing multiple avatars with respective trust ranks computed by a trust ranking algorithm of a server system, according to one embodiment of the invention.

FIG. 3 illustrates a schematic application of the trust ranking, which as previously mentioned provides an indicia of an otherwise unrecognizable characteristic of the first avatar 260, the second avatar 270, and a third avatar 300. In one embodiment, the unrecognizable characteristic may be representative of a degree of trustworthiness the first avatar should place in communications with the second avatar. Doing so may help to identify potential spammers. In operation, the system 120 stores account information for the first avatar 260, second avatar 270 and third avatar 300 in the user index 105 once each user opens an account corresponding to a respective one of the avatars 260, 270, 300. A trust ranking algorithm 306 executed by the system 120 takes data from the interaction records 106 that are related to interactions between the avatars 260, 270, 300 (and other avatars) correlated within the user index 105 and computes first, second and third trust ranks 360, 370, 301 applied to respectively the first, second and third avatars 260, 270, 300. That is, the trust ranking algorithm 306 evaluates interactions between the avatars, including the actions in which a given avatar participates, to assign a trust ranking to each avatar. In one embodiment, users may rely on the trust rankings assigned to an avatar they interact with to determine if a reply is worthwhile or if information being provided is accurate. Examples of criteria used by the trust ranking algorithm 306 include conversational content 308, interaction level 310, dialogue repetition 312 and peer feedback 314, as explained in greater detail below.

In one embodiment, the trust ranking algorithm 306 assigns an initial trust rank to an account for each new user account registered with the system. Each user may be assigned (or may generate) an account to give that user a presence within the virtual world. Subsequently, as the user causes their avatar to interact with the virtual world, the trust ranking may increase or decrease from the initial trust rank based on an iterative analysis of the criteria used by the trust ranking algorithm 306. By way of example, since correlations may be reversed and relative values are provided for explanation purposes only, increases in the trust rank may correspond to a higher trustworthiness for an avatar and a lower likelihood of that avatar being a spammer. Illustratively, the first avatar 260 is shown with a first trust rank 360 of ninety. Assume that this value represents an established user with prior history indicative of the user being legitimate. In contrast, the second avatar 270 lacks any data within the interaction records 106 and hence has a second trust rank 370 of twenty-five, for example, that is unchanged from the initial trust rank. Further, the user for the third avatar 300 represents a spammer, which has been identified as such by a trust rank lowered from the initial trust rank (twenty-five) to the third trust rank 301 of five.

For some embodiments, the system 120 may disable the account for the third avatar 300 upon the third trust rank 301 reaching a threshold value selected for suspected spammers. For example, assume a threshold value set to ten, in such a case, the accounts for the first and second avatars 260, 270 with the first and second trust ranks 360, 370 are above the threshold value remain active in the user index 105 as denoted by checked markings. In contrast, the "X" notation for the third avatar 300 in the user index 105 reflects that this account has been disabled, preventing the third avatar 300 from appearing in the user display 200 shown in FIG. 2. In one embodiment, the user of the third avatar 300 may need to follow a process to reactivate the account prior to re-entering the virtual world.

Figure 4:
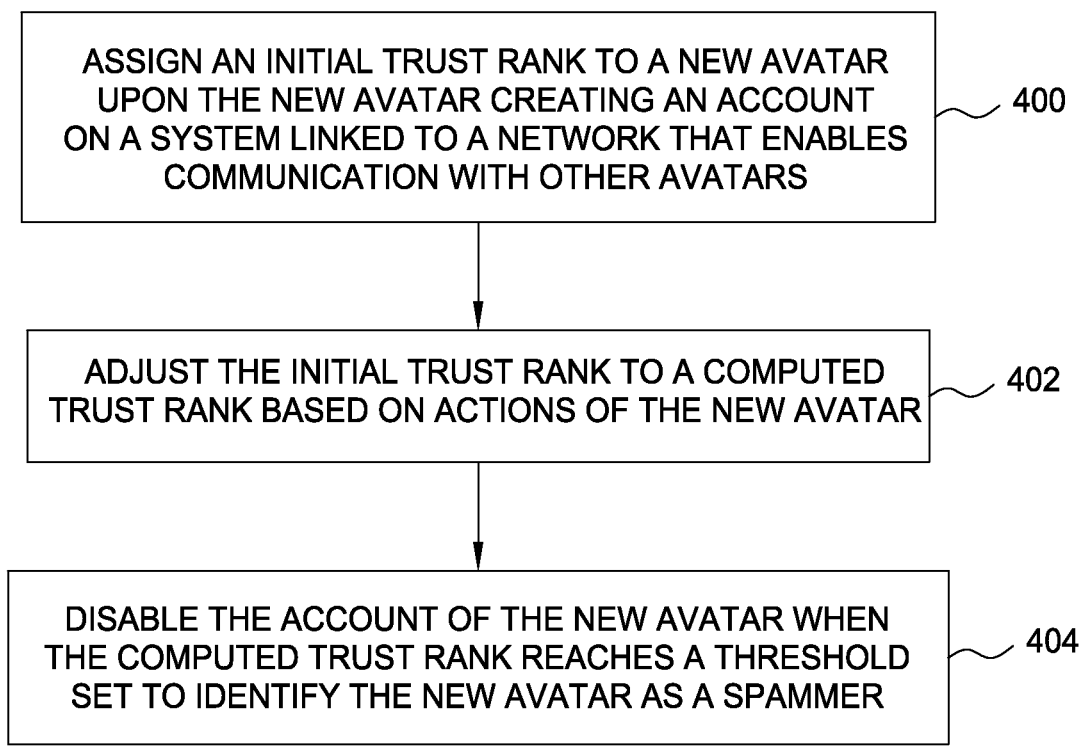
FIG. 4 is a flow diagram illustrating a method of monitoring for spammers, according to one embodiment of the invention.

FIG. 4 shows a flow diagram illustrating a method for monitoring avatars within a virtual environment to identify spammers, according to one embodiment of the invention. At step 400, an initial trust rank may be assigned to a new avatar upon a user creating an account for use on a system linked to a network that enables communication with other avatars (i.e., when a user creates a new account (or new avatar) used to establish a presence within a virtual world). Evaluation step 402 includes adjusting the initial trust rank to a trust rank based on actions of the new avatar. The adjusting may take place over an extended monitoring period of time and incorporate multiple actions such that the computed trust rank is iteratively updated. Disabling the account of the new avatar occurs when the trust rank reaches a threshold set to identify the new avatar as a spammer, at identification step 404. The adjusting occurs such that if the new avatar created at step 400 represents a legitimate user, the trust rank should not reach the threshold in identification step 404.

In some embodiments, a threshold can be provided which users may set such that other avatars with trust ranks outside the threshold cannot communicate with the avatars of the users that have set the threshold. This setting of the threshold can be a global setting or a variable setting based on location of the avatars within the virtual world. Further, limitations may permit a new avatar to only be able to converse with avatars having similar trust ranks unless the avatars accept requests to chat or are in buddy lists. These limitations may ensure that new avatars cannot spam avatars of more established users until being detected, while providing the new avatars with probationary type abilities sufficient to allow interactions necessary for analysis by the trust ranking algorithm 306 in order to improve their trust rank if the new avatar is a legitimate user.

For some embodiments, the trust ranking of avatars is displayed in the user display 200 shown in FIG. 2 next to respective avatars so that a user may know the trust ranking of the avatars in making decisions about the avatars. If the user is the first avatar 260, then the first trust ranking 360 need not be displayed. However, displaying of the second trust ranking 370 in connection with displaying of the second avatar 260 in the user display 200 may help inform the user that the second avatar 260 is a new user that maybe should not be trusted. The second trust rank 370 may always be visible or only become visible upon viewing, clicking or attempting to interact with the second avatar 270.

Figure 5:
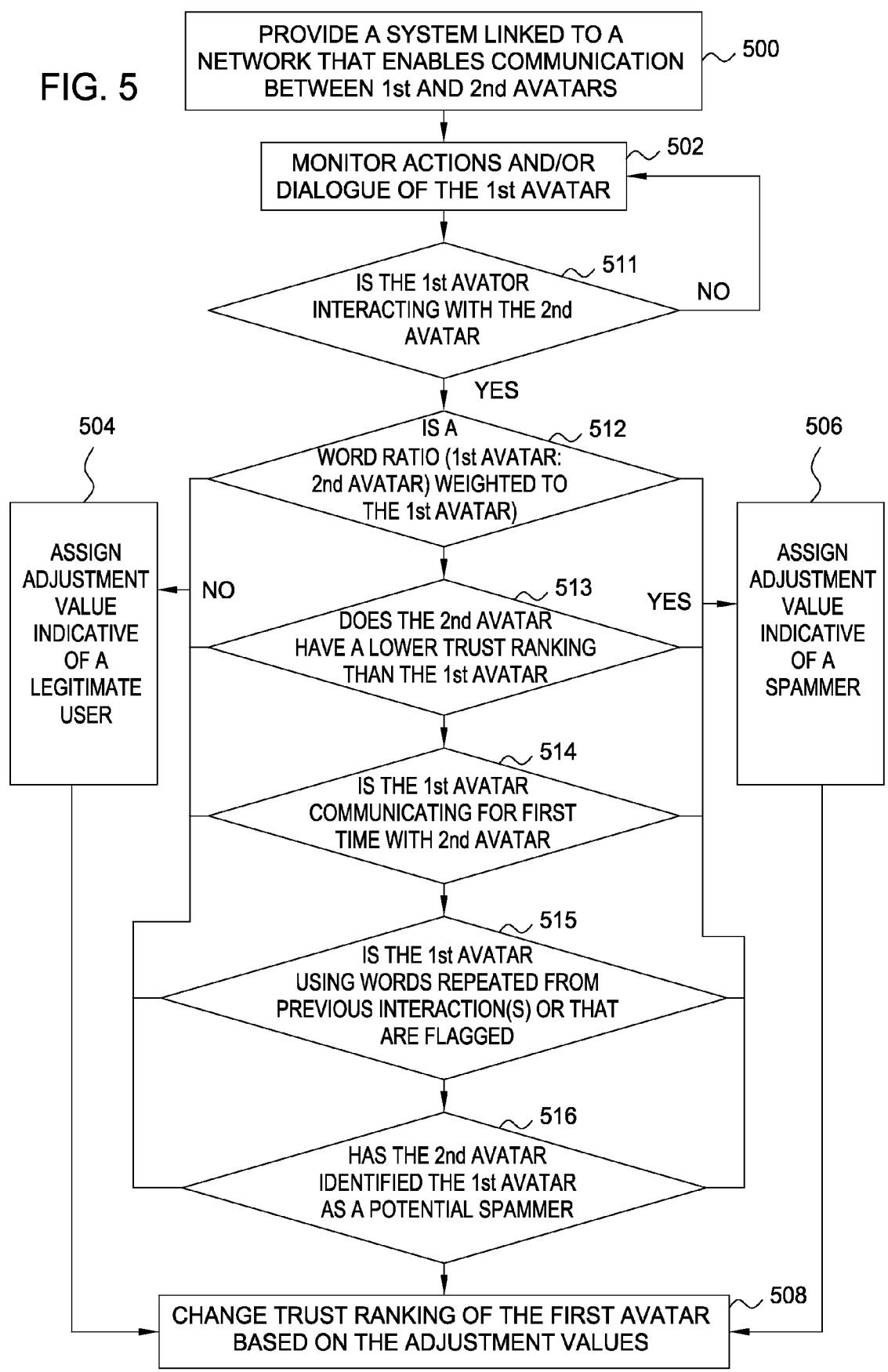
FIG. 5 is a flow diagram illustrating a trust ranking assessment process, according to one embodiment of the invention.

FIG. 5 illustrates an exemplary trust ranking assessment process that, with reference to FIG. 3, further explains use of the conversational content 308, interaction level 310, dialogue repetition 312 and peer feedback 314 as criteria for the trust ranking algorithm 306. Setup step 500 includes providing a system linked to a network that enables communication between first and second avatars. In recording step 502, monitoring actions and/or dialogue of the first avatar lead to a first inquiry 504 that determines if the first avatar is interacting with the second avatar. If the answer to the first inquiry 504 is no, the monitoring continues until the first avatar interacts with the second avatar.

In one embodiment, second through sixth inquiries 512-516 parse the interaction detected by a yes answer to the first inquiry 511. As worded, a no answer to one of the second through sixth inquiries 512-516 inquiries results in assigning adjustment value indicative of a legitimate user in favoring step 504 whereas a yes answer to one of the second through sixth inquiries 512-516 inquiries results in assigning adjustment value indicative of a spammer in disfavoring step 506. Other inquiries in addition to the second through sixth inquiries 512-516 may be suitable to assign the adjustment values, which may also be assigned without all of the second through sixth inquiries 512-516 inquiries. Since each of the second through sixth inquiries 512-516 may have an independent result, the favoring and disfavoring steps 504, 506 may both be present and represent a composite of the answers to the second through sixth inquiries 512-516. With any of the no and yes answers to the second through sixth inquiries 512-516, the answers as explained further herein may provide graded no or yes responses instead of a binary yes or no to facilitate assigning the adjustment values.

In evaluation step 508, the trust ranking assigned to the first avatar may change, based on the adjustment values. The evaluation step 508 thereby computes the trust ranking to provide an indication about a quality of the first avatar that is not otherwise detectable, e.g., a measure of trustworthiness. The assessment process may return to the recording step 502 to enable continuous updating of the trust ranking in the evaluation step 508.

In one embodiment, regarding the interaction level 310, the second inquiry 512 determines whether a word ratio (defined as number of words communicated by the first avatar versus number of words communicated by the second avatar) is weighted to the first avatar. If the first avatar does all the talking in a conversation and then the conversation is over, this creates a much stronger yes answer to the second inquiry 512 than, for example, when the first avatar has ten more words in a one hundred word conversation or ten percent more words. The stronger yes results in a relatively greater adjustment value in the disfavoring step 506 than this later situation that may result in no adjustment. In other words, equal or near balanced interaction between the first avatar and the second avatar typically means that both parties are actively participating in a conversation. By contrast, few or one word answers indicate less interest by the party that is answering. Mainly one sided conversations occur in spamming since the spammer reaches out often, randomly and in an unwanted manner making replies short or non-existent. Spammers frequently do not receive replies due to nonsensical context of the talking. In addition, a history of a majority or certain greater percentage of one-sided conversations may further increase strength of the yes answer to the second inquiry 512.

The third inquiry 513 determines if the second avatar has a lower trust ranking than the first avatar. If the first avatar interacts with the second avatar that has a higher rank and the second avatar interacts back, the interaction tends to indicate that the first avatar is legitimate. Further, the third inquiry 513 prevents the first avatar from gaining credentials without basis as a result of interactions with other spammers that would have poor trust rankings.

Regarding the fourth inquiry 514, analyzing patterns in who the first avatar converses with offers useful information. A spamming avatar is likely to approach a large number of random avatars but have little or no repeat interaction with any of them. By contrast, a legitimate user more likely approaches fewer random avatars and has several close relationships evidenced by repeat interactions with certain avatars. To capture these patterns, the fourth inquiry 514 resolves whether the first avatar is communicating for a first, second or more times with the second avatar. While repeat interactions with the second avatar result in a no answer to the fourth inquiry 514, a yes answer leads to assigning the adjustment value indicative of a spammer in the disfavoring step 506. A historical imbalance of yes answers to the fourth inquiry 514 may provide a stronger yes and hence a relatively greater adjustment value in the disfavoring step 506.

With reference to the conversational content 308 and dialogue repetition 312 represented in FIG. 3, the fifth inquiry 515 ascertains if the first avatar is using words repeated from previous interactions or that are flagged. That is, the first avatar keeps repeating the same message (or variation of a message) to other avatars. For some embodiments, conversational content of the second avatar may also be monitored and reflect on the first avatar. For example, words flagged as relating to emotions, interest and family in conversations back from the second avatar show indications that the first avatar is a legitimate user. Words on generic topics such as the weather lack interest and tend to be used by spammers so that such words may be the flagged ones that can result in a yes answer to the fifth inquiry 515. Moreover, using one set of words when communicating corresponds to more likely behavior of a spammer.

The sixth inquiry 516 corresponds to the peer feedback 314 represented in FIG. 3. The second avatar may attempt to converse with the first avatar and receive irrelevant context or repeat sentences making the second avatar assume that the first avatar must be a spammer. Notification by the second avatar to the system that the first avatar is a potential spammer provides an affirmative response to the sixth inquiry 516 thereby assigning the adjustment value indicative of a spammer in the disfavoring step 506. In some embodiments, the affirmative response to the sixth inquiry flags the first avatar and may trigger monitoring or increased monitoring of the first avatar.

Any of the second through sixth inquiries 512-516 may be linked or associated with one another. For example, particular relevance may occur with two yes answers such as when the first avatar repeats words determined by the fifth inquiry 515 in conjunction with the first avatar receiving short or no responses evidenced by the second inquiry 512. The adjustment indicative of a spammer that is assigned in the disfavoring step 506 may be greater for such combinations than a summation of respective independent yes answers.

As an exemplary scenario in view of aforementioned aspects, the second avatar 270 shown in FIG. 2 may represent a spammer. The second avatar 270 approaches the first avatar 260 and says "store 220 is overpriced." The first avatar 260 hears the comment but does not respond. The second avatar 270 then goes to other avatars and makes another comment promoting a competitor of the store 220. This spamming hinders the virtual world and has a negative impact on business of the store 220. The system 120 illustrated in FIGS. 1 and 3 captures and parses the text of the first and second avatar 260, 270 for content and length as described herein in order to assess that the second avatar 270 is spamming. In particular, the second avatar 270 talks disproportionately about "the store" (i.e., store 220) resulting in a repetition in word-use that provides a basis for, over time, diminishing the second trust rank 370 of the second avatar 270. Similarly, lack of response from the first avatar 260 and lack of repeat interaction with the first avatar 260 among the interactions by the second avatar 270 may further diminish the second trust rank 370 of the second avatar 270.

While the foregoing is directed to embodiments of the present invention, other and further embodiments of the invention may be devised without departing from the basic scope thereof, and the scope thereof is determined by the claims that follow.

What is claimed is:

1. A computer-implemented method of evaluating actions of a first avatar in a virtual environment, comprising:
   assigning, by operation of one or more computer processors, an initial trust rank to the first avatar upon the first avatar creating an account on a system linked to a network that enables communication with other avatars within the virtual environment;
   executing a spam detection module to programmatically monitor one or more interactions between the first avatar and at least a second avatar;
   adjusting, by the spam detection module, the initial trust rank to a computed adjusted trust rank based on the interactions that are monitored; and
   disabling, by the spam detection module, the account of the first avatar when the computed adjusted trust rank reaches a specified threshold, wherein upon disabling the account of the first avatar, the first avatar is not visible to any avatars in the virtual environment.

2. The computer-implemented method of claim 1, wherein adjusting the initial trust rank is based on content and length of the monitored interactions between the first avatar and the second avatar.

3. The computer-implemented method of claim 1, wherein adjusting the initial trust rank is based on comparing number of words used by the first avatar to number of words used by the second avatar in a conversation.

4. The computer-implemented method of claim 1, wherein adjusting the initial trust rank is based on repetitions in the monitored interactions of the first avatar.

5. The computer-implemented method of claim 1, further comprising:
   feedback from the second avatar with respect to the interactions of the first avatar; and
   upon receiving feedback from the second avatar, adjusting, by the spam detection module, the initial trust rank to a computed trust rank based on the feedback received from the second avatar.

6. The computer-implemented method of claim 1, further comprising displaying the computed trust rank on a user display, wherein the one or more interactions between the first avatar and at least the second avatar are monitored without user input.

7. The computer-implemented method of claim 1, wherein programmatically monitoring one or more interactions between the first avatar and at least a second avatar includes identifying that the first avatar is communicating by repeating a set of one or more words to multiple avatars.

8. The computer-implemented method of claim 1, further comprising limiting the interactions of the first avatar until the computed trust rank reaches a second specified threshold.

9. The computer-implemented method of claim 1, further comprising blocking communication of the first avatar with at least one other avatar according to criteria for the computed trust rank as set by the at least one other avatar.

10. A computer program product, comprising:
    a non-transitory computer-readable storage medium having computer-readable program code embodied therewith, the computer-readable program code executable by a processor to perform an operation to evaluate actions of a first avatar in a virtual environment, the operation comprising:
    assigning an initial trust rank to the first avatar upon the first avatar creating an account on a system linked to a network that enables communication with other avatars within the virtual environment;
    executing a spam detection module to programmatically monitor one or more interactions between the first avatar and at least a second avatar;
    adjusting, by the spam detection module, the initial trust rank to a computed adjusted trust rank based on the interactions that are monitored; and
    disabling, by the spam detection module, the account of the first avatar when the computed adjusted trust rank reaches a specified threshold, wherein upon disabling the account of the first avatar, the first avatar is not visible to any avatars in the virtual environment.

11. The computer program product of claim 10, the operation further comprising displaying the computed adjusted trust rank on a user display, wherein the one or more interactions between the first avatar and at least the second avatar are monitored without user input.

12. A system, comprising:
one or more computer processors; and
a memory containing a program, which when executed by the one or more computer processors is configured evaluate actions of a first avatar in a virtual environment, the operation comprising:
  assigning an initial trust rank to the first avatar upon the first avatar creating an account on a system linked to a network that enables communication with other avatars within the virtual environment;
  monitoring, by a spam detection module, one or more interactions between the first avatar and at least a second avatar;
  adjusting, by the spam detection module, the initial trust rank to a computed adjusted trust rank based on the interactions that are monitored; and
  disabling, by the spam detection module, the account of the first avatar when the computed adjusted trust rank reaches a specified threshold, wherein upon disabling the account of the first avatar, the first avatar is not visible to any avatars in the virtual environment.

13. The system of claim 12, wherein adjusting the initial trust rank is based on content and length of the monitored interactions between the first avatar and the second avatar.

14. The system of claim 12, wherein adjusting the initial trust rank is based on repetitions in the monitored interactions of the first avatar.

15. The system of claim 12, wherein adjusting the initial trust rank includes comparing number of words used by the first avatar to number of words used by the second avatar in a conversation.

16. The system of claim 12, wherein monitoring the first avatar is triggered by feedback from a third avatar.

17. The system of claim 12, the operation further comprising displaying the trust rank on a user display, wherein the one or more interactions between the first avatar and at least the second avatar are monitored without user input.

18. The system of claim 12, wherein adjusting the trust rank occurs based on number of words used by the first avatar in the interaction being greater than number of words used by the second avatar in the interaction.

19. The system of claim 12, the operation further comprising limiting communications by the first avatar, wherein the trust ranking is applied against a set criterion to determine which communications are limited.

* * * * *